United States Patent [19]

Loew et al.

[11] 4,064,136
[45] Dec. 20, 1977

[54] PROCESS FOR THE MANUFACTURE OF BENZOXAZOLE, BENZTHIAZOLE AND BENZIMIDAZOLE DERIVATIVES

[75] Inventors: Peter Loew, Munchenstein; Hansrudolf Schwander, Riehen; Haukur Kristinsson, Bottmingen, all of Switzerland

[73] Assignee: Ciba-Geigy AG, Basel, Switzerland

[21] Appl. No.: 704,896

[22] Filed: July 13, 1976

[30] Foreign Application Priority Data

July 21, 1975 Switzerland .................. 9503/75

[51] Int. Cl.$^2$ .................. C07D 277/64; C07D 203/56; C07D 235/12; C07D 235/14
[52] U.S. Cl. .................. 260/304 C; 260/158; 260/293.57; 260/293.58; 260/293.6; 260/307 D; 260/309.2; 260/465.5 R; 260/561 A; 260/562 N; 548/326; 548/330; 560/168; 560/142; 560/145; 560/143; 560/144
[58] Field of Search .......... 260/304 D, 307 D, 309.2, 260/293.57, 293.58, 293.6

Primary Examiner—Richard J. Gallagher
Attorney, Agent, or Firm—Karl F. Jorda; Edward McC. Roberts; Prabodh I. Almaula

[57] ABSTRACT

Process for the manufacture of a heterocyclic compound of the formula I

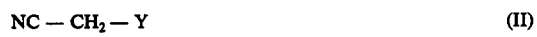

(I)

in which Y denotes a —CN, —COOR' or

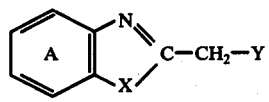

group, in which R' can be an optionally substituted alkyl or aryl radical and R" and R'" independently of one another can have the same meaning as R' or can be hydrogen or, conjointly with the nitrogen atom, can form a heterocyclic 5-membered or 6-membered ring and X denotes a —S— or —O— atom or a —NR"— group and the ring A can carry non-ionic substituents or optionally substituted fused rings, wherein a nitrile of the formula II $$NC-CH_2-Y \qquad (II)$$

is reacted, in organic solvents, with a lower alcohol of the formula III $$R-OH \qquad (III)$$

using a molar ratio of nitrile to alcohol of 1:0.9 to 1:1.2, in the presence of an anhydrous strong acid at temperatures of $-10°$ to $+40°$ C to give an imino-ether salt of the formula IV

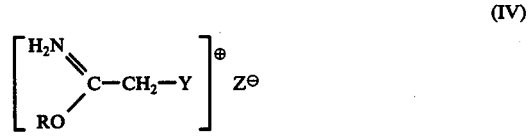

(IV)

and the resulting imino-ether salt is subjected, without intermediate isolation thereof, to a condensation reaction with an aromatic amine of the formula V

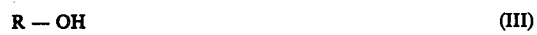

(V)

using a molar ratio of nitrile to amine of the formula V of 1:0.8 to 1:1.2, at temperatures of 0° to 120° C to give compounds of the formula I, and in the formulae II to V, A, Y and X have the meaning indicated under formula I, R denotes a lower alkyl radical and Z$^-$ denotes an anion of a strong acid.

8 Claims, No Drawings

PROCESS FOR THE MANUFACTURE OF BENZOXAZOLE, BENZTHIAZOLE AND BENZIMIDAZOLE DERIVATIVES

It is known that, in order to manufacture heterocyclic compounds of the formula I

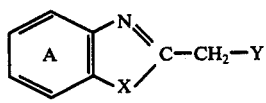
(I)

wherein Y denotes a —CN, —COOR' or

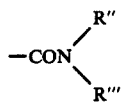

group, in which R' can be an optionally substituted alkyl or aryl radical and R" and R''' independently of one another can have the same meaning as R' or can be hydrogen or, conjointly with the nitrogen atom, can form a heterocyclic 5-membered or 6-membered ring and X denotes a —S- or —O— atom or a —NR"— group and the ring A can carry non-ionic substitutent or optionally substituted fused rings, imino-ethers are subjected to a condensation reaction with o-amino-phenols, -thiophenols or -anilines. These known processes have the disadvantage that they are carried out in separate process steps: 1. manufacture of the imino-ether from aliphatic nitriles, 2. isolation of the imino-ester by filtering off and drying and 3. a condensation reaction of this compound and a o-amino-phenol, -thiophenol or -aniline.

The imino-ether compounds, which are not without risk from the ecological point of view, can be handled only when safety measures are carefully observed, since they are highly susceptible to hydrolysis and very sensitive to heat. Therefore, because the reaction sequence is in separate steps and because of their tendency to decompose, the manufacture of these compounds requires a considerable expenditure on apparatus.

It has now been found that compounds of the above-mentioned formula I can be manufactured with elimination of the difficulties described above when a nitrile of the formula II

  (II)

is reacted, in organic solvents, with a lower alcohol of the formula III

R —OH  (III)

using a molar ratio of nitrile to alcohol of 1:0.9 to 1:1.2, in the presence of an anhydrous strong acid at temperatures of −10° to +40° C to give imino-ether salts of the formula IV (IV)

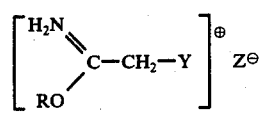

and the resulting imino-ether salts are subjected, without intermediate isolation thereof, to a condensation reaction with aromatic amines of the formula V

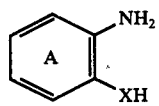
(V)

using a molar ratio of nitrile to amine of the formula V of 1:0.8 to 1:1.2, at temperatures of 0° to 120° C to give compounds of the formula I, and in the formulae II to V, A, Y and X have the meaning indicated under formula I, R denotes a lower alkyl radical and $Z^-$ denotes an anion of a strong acid.

With this procedure, the isolation of the imino-ester compound is dispensed with and, apart from economic and ecological advantages, this also results in savings in the starting materials and in energy. Safety can be further increased by carrying out the further processing (condensation reaction) of the imino-ester, which is formed as an intermediate in a closed apparatus.

If R', R" and R''' denote an optionally substituted alkyl radical, this can be straight-chain or branched and contain up to 18 carbon atoms. Possible substitutents are, for example, acyloxy, alkoxy and halogen.

If R', R" and R''' denote an aryl radical, this is, above all, a phenyl radical, which can contain non-ionic substituents. Examples which may be mentioned of non-ionic substituents of this phenyl radical, and also of the benzo radical A, are: lower, optionally substituted alkyl, lower alkoxy, halogen, especially chlorine or bromine, nitro, cyano, carboxylic acid esters or sulphonic acid amides.

Nitriles of the formula II which can be used are cyanoacetamide and, in particular, cyanoacetic acid esters and, above all, malonodinitrile.

The lower alcohols of the formula III which are used are preferably those which have 1 to 4 carbon atoms, especially methanol and ethanol.

Possible aromatic amines of the formula V which can be used according to the invention are o-diaminobenzenes and in particular o-aminophenols and above all o-aminothiophenols. Specific examples which may be mentioned are: o-aminothiophenol, o-phenylenediamine, o-aminophenol, o-aminohydroxytoluene, o-aminohydroxyxylene, o-aminochlorophenol, o-aminoethylphenol, o-aminodichlorophenol, o-amino-tert.-butylphenol, o-aminophenylphenol, o-aminonaphthol, o-aminocyanoethylphenol, ethoxycarbonylethyl-o-aminophenol, ethoxycarbonylethyl-o-aminocresol, ethyl o-aminohydroxybenzoate, methoxyethyl o-aminohydroxybenzoate, o-aminohydroxytoluic acid esters, o-aminonitrophenol, o-aminochlorothiophenol, o-aminodichlorothiophenol, o-aminomethylthiophenol, o-aminodimethylthiophenol, o-aminonitrothiophenol, o-aminoethylthiophenol, o-aminochloromethylthiophenol, o-aminothionaphthol, o-diaminotoluene, o-diaminoxylene, nitro-o-phenylenediamine, chloro-o-phenylenediamine, dichloro-o-phenylenediamine, o-diaminobenzoic acid esters, o-diaminobenzonitrile, o-diaminonaphthalene, o-diaminobenzenesulphonamide and o-aminophenolsulphamide.

Possible organic solvents, which can be used as the reaction medium in the process according to the invention, are, above all, aprotic solvents, for example aromatic hydrocarbons, such as benzene, toluene or xylene, aliphatic and aromatic chlorinated hydrocarbons, such as carbon tetrachloride, trichloroethylene, ethylene chloride, methylene chloride, chloroform, trichloroethane, tetrachloroethane, perchloroethylene, monochlorobenzene or dichlorobenzene, and ethers, such as dioxane, tetrahydrofurane or ethylene glycol dimethyl ether and the like. Mixtures of the said solvents can also be used. The amount of solvent which is used as the reaction medium depends on the reaction substrate employed in the particular case and is chosen solely from the point of view of process engineering (for example good stirrability) and economics (favourable space-time yield).

Anhydrous strong acids which can be used are both inorganic acids, such as, for example, gaseous hydrogen halide acids, especially gaseous hydrochloric acid, and organic acids, such as, for example, p-tolunesulphonic acid. The anhydrous strong acids are advantageously used in amounts of 1 to 1.3 equivalents. The preferred anhydrous strong acid is gaseous hydrochloric acid, since, because of its poor solubility in aprotic solvents, the excess of this acid can easily be blown out with nitrogen.

The one pot reaction can be carried out in simple reaction vessels, which have a reflux condenser and stirrer, without applying pressure or can be carried out under pressure in stirred autoclaves. In detail, the procedure is as follows:

The nitriles used as the starting components are dissolved in an organic solvent in a reaction vessel and, optionally, it is also possible for an excess of the alcohol which is required for the reaction to serve as the solvent. Preferably, the starting components are dissolved in a mixture consisting of the alcohol for the reaction and an organic solvent as the reaction medium and the sequence of the addition is chosen depending on which component has the better solubility in the particular medium. Thereafter, whilst stirring the mixture at a temperature of −10° to +40° C, and preferably 0° to 30° C, dry hydrogen chloride gas is passed in, or another anhydrous strong organic acid is added to, the reaction mixture and the latter is stirred for several hours. When the reaction has ended, the aromatic amine is added to the reaction mixture and the latter is again stirred for several hours at temperatures between 0° and 120° C, and preferably at 20° to 80° C, until the condensation reaction has ended.

The resulting product is then worked up by known customary methods, for example by distillation, by concentrating the solvent, filtering off the product and washing or by adding water or an aqueous acid, which results in the formation of two phases, separating the phases and, for example, evaporating the organic phase to dryness.

Pure products are obtained, in yields of 60 to 100%, direct or after a purification operation, for example by distillation or recrystallisation.

The solvents used can be recovered virtually completely and re-used, after drying, for a new batch.

Because of the advantageous stoichiometric ratio of the reactants and because the solvent used as the reaction medium is recovered, hardly any waste products are formed.

The compounds manufactured by the process according to the invention are in themselves known and are, for example, valuable intermediate products for the manufacture of disperse, cationic and anionic dyestuffs. Examples of such compounds which may be mentioned specifically are: benzoxazolylacetonitrile, benzoxazolylacetic acid esters, benzoxazolylacetamides, methylbenzoxazolylacetonitrile, dimethylbenzoxazolylacetonitrile, chlorobenzoxazolylacetonitrile, tert.-butylbenzoxazolylacetonitrile, phenylbenzoxazolyacetonitrile, naphthoxazolylacetonitrile, cyanoethylbenzoxazolylacetonitrile, ethoxycarbonylethylbenzoxazolylacetonitrile, ethoxycarbonylethylmethylbenzoxazolylacetonitrile, ethoxycarbonylbenzoxazolylacetonitrile, ethoxycarbonylmethylbenzoxazolylacetonitrile, nitrobenzolylacetonitrile, dichlorobenzoxazolylacetonitrile, methylbenzoxazolylacetic acid esters, benzthiazolylacetonitrile, chlorobenzthiazolylacetonitrile, dichlorobenzthiazolylacetonitrile, methylbenzthiazolylacetonitrile, dimethylbenzthiazolylacetonitrile, nitrobenzthiazolylacetonitrile, chloromethylbenzthiazolylacetonitrile, naphthiazolylacetonitrile, benzthiazolylacetic acid esters, methylbenzthiazolylacetic acid esters, benzthiazolylacetamides, benzimidazolylacetonitrile, methylbenzimidazolylacetonitrile, dimethylbenzimidazolylacetonitrile, chlorobenzimidazolylacetonitrile, nitrobenzimidazolylacetonitrile, ethoxycarbonylbenzimidazolylacetonitrile, cyanobenzimidazolylacetonitrile, naphthimidazolylacetonitrile, benzimidazolylacetic acid esters and benzimidazolylacetamides.

The examples which follow illustrate the procedure of the process according to the invention, without restricting it to these examples. The temperatures are given in degrees Centigrade. Parts denote units by weight.

EXAMPLE 1

16.5 parts of malonodinitrile are dissolved in 11.5 parts of absolute ethanol and 100 parts of trichloroethylene are added. 12 parts of gaseous hydrogen chloride are passed in at room temperature, with the exclusion of moisture, and the resulting suspension is stirred for a further 16 hours at room temperature. The excess of hydrogen chloride is driven off by passing in nitrogen. 31 parts of o-aminothiophenol are added dropwise in the course of 30 minutes under a nitrogen atmosphere. During this addition the temperature rises to 50°. After stirring the reaction mixture at 60° for 1 hour, it is cooled to room temperature and 100 parts of water are added. The organic phase is separated off and evaporated to dryness.

In this way, 43 parts of benzthiazolylacetonitrile are obtained as an almost colourless powder which, when recrystallised from perchloroethylene, has a melting point of 102°.

EXAMPLE 2

26.5 parts of malonodinitrile are dissolved in 18.5 parts of absolute ethanol and 400 parts of dry chloroform are added. 15 parts of dry hydrogen chloride gas are passed in at room temperature, with the exclusion of moisture, and the resulting suspension is stirred for 16 hours at 0° to 5°. 49.2 parts of m-amino-p-cresol are then added and the reaction mixture is stirred for 24 hours at room temperature. The suspension is filtered, the residue is washed four times with chloroform and the filtrates are evaporated to dryness.

65.3 parts of methylbenzoxazolylacetonitrile are obtained as a colourless powder which has a melting point of 85° to 86°.

EXAMPLE 3

16.5 parts of malonodinitrile are dissolved in 11.5 parts of absolute alcohol and 100 parts of dioxane and 9 parts of dry hydrogen chloride are added at 0° to 5°, with the exclusion of moisture. The resulting suspension is stirred for 9 hours at 0° to 5° and a solution of 27 parts of o-phenylenediamine in 100 parts of dioxane is then added. The mixture is stirred for 15 hours at room temperature and the solvent is then distilled off in vacuo. The residue is stirred with water and the product is filtered off, washed with water and dried.

35 parts of benzimidazolylacetonitrile, which has a melting point of 189°, are obtained.

EXAMPLE 4

19 parts of hydrogen chloride gas are passed into 56.5 parts of ethyl cyanoacetate, 23 parts of absolute ethanol and 150 parts of tetrachloroethane at 20° to 25°, with the exclusion of moisture. The mixture is stirred for 3 hours at 0° to 5° and 62.5 parts of o-amino-thiophenol are then added under nitrogen. The temperature is kept at 25° to 30° by cooling. After stirring for 18 hours at room temperature, 2 N hydrochloric acid is added to the mixture and the resulting mixture is shaken well. The organic phase is separated off, wasehd with water until neutral and concentrated by distillation and the residue, that is to say 92 parts of a yellow liquid, is distilled under a high vacuum. Pure ethyl benzthiazolylacetate distils off at 120°/0.04 mm.

Further compounds of the formula

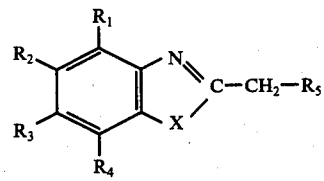

which are obtained according to this instructions of Examples 1 to 4 using equivalent amounts of the corresponding reactants, are listed in the Table which follows.

TABLE

| Example | $R_1$ | $R_2$ | $R_3$ | $R_4$ | $R_5$ | X |
|---|---|---|---|---|---|---|
| 5 | H | H | H | H | CN | O |
| 6 | H | $CH_3$ | H | H | CN | O |
| 7 | H | $CH_3$ | H | $CH_3$ | CN | O |
| 8 | H | Cl | H | H | CN | O |
| 9 | H | $(CH_3)_3C-$ | H | H | CN | O |
| 10 | H | $(CH_3)_3CCH_2C(CH_3)_2-$ | H | H | CN | O |
| 11 | H | phenyl- | H | H | CN | O |
| 12 | H | H | phenyl- | H | CN | O |
| 13 | $R_1 + R_2 =$ $-CH=CH-CH=CH-$ | | H | H | CN | O |
| 14 | H | $NCCH_2CH_2-$ | H | H | CN | O |
| 15 | H | $C_2H_5OCOC_2H_4-$ | H | H | CN | O |
| 16 | H | $C_2H_5OCOC_2H_4-$ | H | $CH_3$ | CN | O |
| 17 | H | $CH_3OC_2H_4OCOC_2H_4-$ | H | H | CN | O |
| 18 | H | $CH_3OC_2H_4OCOC_2H_4-$ | H | $CH_3$ | CN | O |
| 19 | H | $C_2H_5OOC-$ | H | H | CN | O |
| 20 | H | $CH_3OC_2H_4OOC-$ | H | H | CN | O |
| 21 | H | $CH_3$ | H | $COOC_2H_5$ | CN | O |
| 22 | H | $CH_3$ | H | $COOC_2H_4OCH_3$ | CN | O |
| 23 | H | $NO_2$ | H | H | CN | O |
| 24 | H | Cl | H | Cl | CN | O |
| 25 | H | H | H | H | $COOC_2H_5$ | O |
| 26 | H | $CH_3$ | H | H | $COOC_2H_5$ | O |
| 27 | H | H | H | H | $CON(CH_3)_2$ | O |
| 28 | H | H | H | H | $CONHCH_3$ | O |
| 29 | H | Cl | H | H | CN | S |
| 30 | H | H | Cl | H | CN | S |
| 31 | Cl | H | Cl | H | CN | S |
| 32 | H | Cl | H | Cl | CN | S |
| 33 | H | $CH_3$ | H | H | CN | S |
| 34 | H | H | H | $CH_3$ | CN | S |
| 35 | H | H | $CH_3$ | H | CN | S |
| 36 | H | $NO_2$ | H | H | CN | S |
| 37 | H | H | $NO_2$ | H | CN | S |
| 38 | $CH_3$ | H | Cl | H | CN | S |
| 39 | $R_1 + R_2 =$ $-CH=CH-CH=CH-$ | | H | H | CN | S |
| 40 | H | H | $R_3 + R_4 =$ $-CH=CH-CH=CH-$ | | CN | S |
| 41 | H | H | H | H | $CON(CH_3)_2$ | S |
| 42 | H | H | H | H | CON H (cyclohexyl) | S |
| 43 | H | H | H | H | $CONHC_2H_5$ | S |
| 44 | H | $CH_3$ | H | H | CN | NH |
| 45 | H | $NO_2$ | H | H | CN | NH |
| 46 | H | Cl | H | H | CN | NH |

TABLE-continued

| Example | R₁ | R₂ | R₃ | R₄ | R₅ | X |
|---|---|---|---|---|---|---|
| 47 | H | Cl | Cl | H | CN | NH |
| 48 | H | CH₃ | CH₃ | H | CN | NH |
| 49 | H | COOC₂H₅ | H | H | CN | NH |
| 50 | H | CN | H | H | CN | NH |
| 51 | R₁ + R₂ = —CH=CH—CH=CH— | | H | H | CN | NH |
| 52 | H | | R₂ + R₃ = —CH=CH—CH=CH— | H | CN | NH |
| 53 | H | H | H | H | COOC₂H₅ | NH |
| 54 | H | NO₂ | H | H | COOC₂H₅ | NH |
| 55 | H | H | H | H | CON(CH₃)₂ | NH |

EXAMPLE 56

3.4 parts of 5-amino-3-methyl-1-phenylpyrazole are diazotised in the customary manner and added dropwise, at 0° to 10°, to a solution of 3.5 parts of benzthiazolylacetonitrile in 30 parts of 80% strength acetic acid. After stirring for a short time, the dye base is precipitated by adding ice and neutralising with sodium hydroxide solution, filtered off, washed with water and dried. 3.6 parts of this dye base are quaternised, at 100°, in chlorobenzene with 3.1 parts of dimethyl sulphate, in the presence of 0.6 parts of magnesium oxide. The precipitate which has separated out is filtered off, washed with chlorobenzene and dried. In this way, 6.1 parts of the dyestuff of the formula

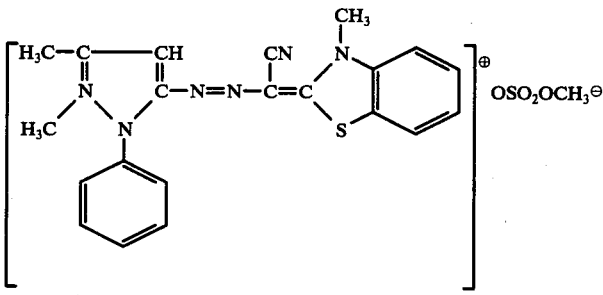

which dyes polyacrylonitrile in yellow shades which have excellent fastness properties, are obtained.

What is claimed is:
1. A process for the manufacture of a heterocyclic compound of the formula

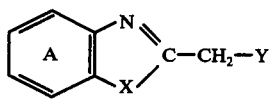

wherein Y is —CN, —COOR' or

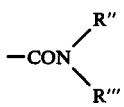

where
R' is alkyl of up to 18 carbon atoms; or is phenyl which is unsubstituted or substituted by lower alkyl, lower alkoxy, chloro, bromo, nitro or cyano;
R" and R'" are independently R', hydrogen, or together with the nitrogen to which they are attached, represent piperidino;
X is —S—, —O—, or —NR"—;
and the benzene ring A is unsubstituted or substituted by lower alkyl, lower alkoxy, chloro, bromo, nitro, cyano, phenyl, 2-cyanoethyl, 2-ethoxycarbonylethyl, 2-(2'-methoxyethoxy)-ethoxycarbonylethyl, ethoxycarbonyl, 2-methoxyethoxycarbonyl or fused phenyl;
wherein a nitrile of the formula

NC—CH₂—Y is reacted in an aprotic organic solvent, with an alcohol of the formula

R—OH where R is a lower alkyl,
in a molar ratio of said nitrile to said alcohol of 1:0.9 to 1:1.2, in the presence of an anhydrous strong acid at temperatures of −10° to +40° C to give an imino-ether salt of the formula

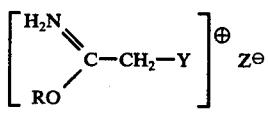

where Z − is the anion of said strong acid, and said imino-ether salt is subjected, without intermediate isolation thereof, to a condensation reaction with an aromatic amine of the formula

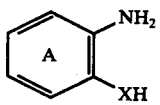

in a molar ratio of said nitrile to said aromatic amine of 1:0.8 to 1:1.2, at temperatures of 0° to 120° C to produce said heterocyclic compound.

2. A process according to claim 1, wherein said nitrile is malonodinitrile or a cyanoacetric acid ester.

3. A process according to claim 2, wherein said nitrile is malonodinitrile.

4. A process according to claim 1, wherein said aromatic amine is an o-aminophenol or an o-aminothiophenol.

5. A process according to claim 4, wherein said aromatic amine is an o-aminothiophenol.

6. A process according to claim 1 wherein said alcohol is methanol or ethanol.

7. A process according to claim 1, wherein said anhydrous strong acid is gaseous hydrochloric acid or a strong organic acid.

8. A process according to claim 7 wherein said anhydrous strong acid is gaseous hydrochloric acid.

* * * * *